US005872447A

United States Patent [19]

Hager, III

[11] Patent Number: 5,872,447
[45] Date of Patent: Feb. 16, 1999

[54] METHOD AND APPARATUS FOR IN-SITU MEASUREMENT OF POLYMER CURE STATUS

[76] Inventor: Nathaniel E. Hager, III, 772 Dorsea Rd., Lancaster, Pa. 17601

[21] Appl. No.: 926,731

[22] Filed: Sep. 10, 1997

[51] Int. Cl.$^6$ ............... G01N 22/00; G01R 27/04
[52] U.S. Cl. ............ 324/71.1; 324/637; 324/642
[58] Field of Search .................. 324/637, 639, 324/640, 642, 643, 646, 663, 690, 71.1; 73/53.01, 54.01, 54.02

[56] References Cited

U.S. PATENT DOCUMENTS

| 4,399,100 | 8/1983 | Zsolnay et al. | 422/62 |
|---|---|---|---|
| 4,423,371 | 12/1983 | Senturia et al. | 324/663 |
| 4,777,431 | 10/1988 | Day et al. | 324/690 |
| 4,779,452 | 10/1988 | Cohen-Tenoudji et al. | 73/54 |
| 5,059,914 | 10/1991 | Lacombe et al. | 324/642 |
| 5,210,499 | 5/1993 | Walsh | 324/71.1 |
| 5,317,252 | 5/1994 | Kranbuehl | 324/71.1 |
| 5,334,941 | 8/1994 | King | 324/637 |
| 5,432,435 | 7/1995 | Strong et al. | 324/71.1 |
| 5,514,965 | 5/1996 | Westwood | 324/642 |
| 5,744,971 | 4/1998 | Chan et al. | 324/643 |
| 5,748,002 | 5/1998 | Scott et al. | 324/637 |

OTHER PUBLICATIONS

Carrozzino et al., "Calorimetric and Microwave Dielectric Monitoring of Epoxy Resin Cure", Polymer Engineering and Science, Mar. 1990, vol. 30, No. 6, pp. 366–373.

*Primary Examiner*—Diep N. Do
*Attorney, Agent, or Firm*—Martin Fruitman

[57] ABSTRACT

An apparatus and a method for determining the cure state of thermosetting polymers using time domain reflectometry. A miniature capacitor is constructed at the end of a coaxial transmission line which is immersed in the curing polymer so that the polymer is the dielectric of the capacitor, and step function voltage pulses are fed to the transmission line, while the reflected signal from the line is monitored. The amplitude and decay characteristics of the reflected signals, which are related to the degree of cure and the viscosity, respectively, are fed to a computer for interpretation and display.

13 Claims, 5 Drawing Sheets

METHOD AND APPARATUS FOR IN-SITU MEASUREMENT OF POLYMER CURE STATUS

BACKGROUND OF THE INVENTION

This invention deals generally with electrical measuring and testing, and more specifically with the determination of the non-electric property of the state of cure of a thermosetting polymer by the use of time domain reflectometry.

The degree of cure of thermosetting polymers is of considerable interest in industry because the cure status determines the strength of a part and also whether it can be subjected to subsequent manufacturing processes. However, since the cure status of the internal portion of a part can not be evaluated visually, considerable effort has been expended to find methods to accurately evaluate the cure state.

Several electrical methods to determine cure state have been used. Among them are the measurement of impedance (U.S. Pat. No. 5,432,435 to Strong et al), reflection of continuous microwave energy (U.S. Pat. No. 5,059,914 to Lacombe et al), and dielectric properties (U.S. Pat. No. 4,777,431 to Day et al). Carrozzino et al have also performed laboratory tests (noted in *Polymer Engineering And Science* March 1990, Vol. 30, No. 6, pp 366) on the use of time domain reflectometry to evaluate the degree of cure. However, Carrozzino concluded that such an approach had poor accuracy and repeatability, and the publication did not disclose the use of in-situ sensors or the measurement of viscosity.

SUMMARY OF THE INVENTION

However, the present invention has demonstrated a time domain reflectometry apparatus which furnishes highly accurate and very repeatable measurements of the viscosity and percent of cure of polymers. The invention combines the simplicity of electrical sensing with miniaturization available from high frequency techniques in a time domain reflectometry measuring device. Such an apparatus is usable for in-situ monitoring of the cure status of composites, and is important for overcoming quality control problems, increasing production speed, and improving the uniformity of composite manufacture, especially in critical structures.

In the preferred embodiment of the invention, a sensor embedded within the part being constructed receives and reflects a fast rise time pulse, and the reflected transient signal relates to the dipole rotation occurring in the microwave frequency range for a particular epoxy dipole. Because of this phenomenon, the reflected signal can be directly related to viscosity and percent of cure. In experimental tests, changes in the signal have been followed during processing and compared to other test methods to establish information in regard to the relationship of the reflected signal to the state of cure and to the viscosity.

The sensor is a miniature capacitor constructed at the end of a miniature transmission line which is immersed in the curing polymer. Step function voltage pulses are fed to the transmission line, and the reflected signal from the transmission line is monitored. The amplitude of the reflected pulse signals, which is related to the degree of cure, and the decay characteristics of the reflected pulse signals, which are related to the viscosity, are then fed to a computer for interpretation and display.

The invention thereby furnishes a real time measurement of the state of cure of the polymer, and the transmission line and sensor, which remain in place after the material is cured, can actually be used with the same signal generator and signal processing system to later check for cracks or discontinuities which might develop in the cured part at a later time.

DETAILED DESCRIPTION OF THE INVENTION

Figure 1:
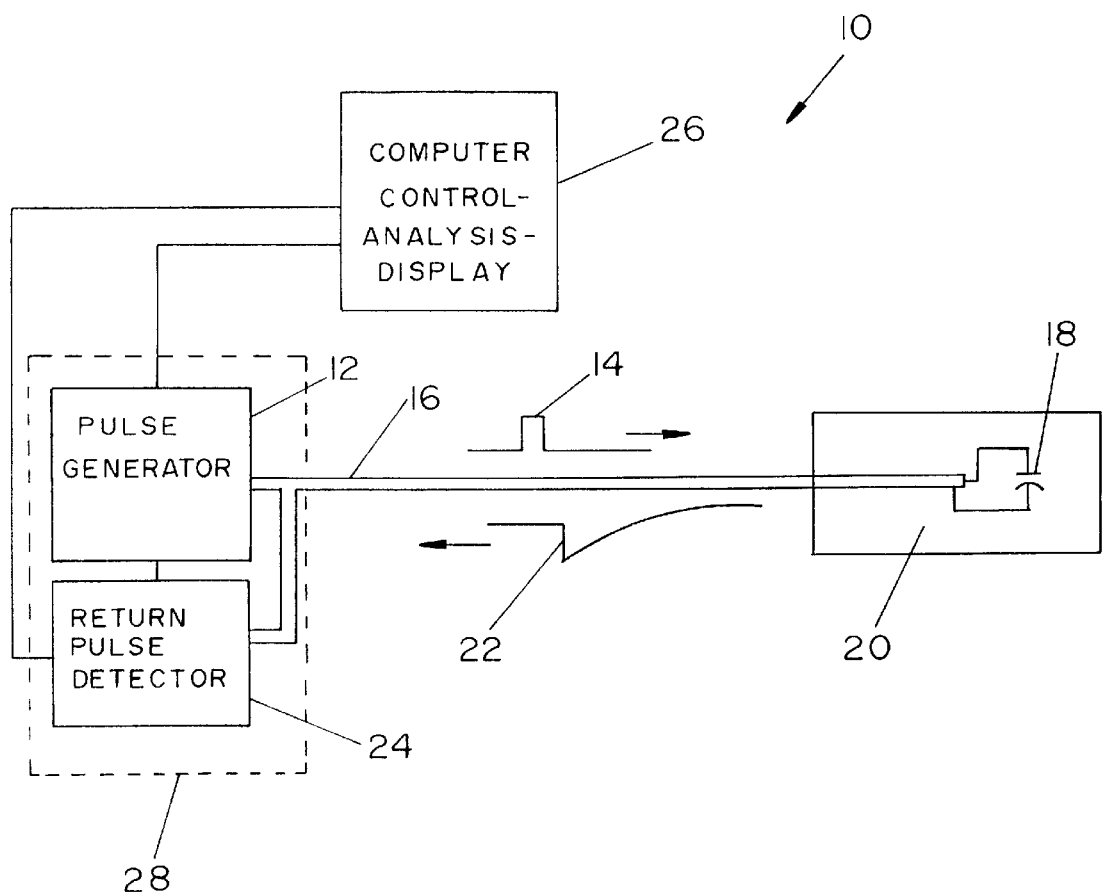
FIG. 1 is a simplified schematic diagram of the preferred embodiment of the invention.

FIG. 1 is a simplified schematic diagram of the preferred embodiment of cure monitoring apparatus 10 of the invention in which pulse generator 12 supplies step function incident pulse 14 to transmission line 16. Capacitor sensor 18 which is located at the remote end of transmission line 16, is immersed within curing polymer 20 and reflects return pulse 22 back to pulse detector 24. The timing of pulse generator 12, the analysis of return pulse 22, and the display of the test parameters and results are performed by computer 26.

The parameters of the reflected pulse which indicate the viscosity and cure status of polymers are the variations in the decay time for viscosity and variations of the amplitude for percent of cure. These are affected by the dipole rotation spectrum of the polymer. Changes in the reflected pulse parameters are actually indications of a more sophisticated change in frequency characteristics of the polymer, so that measurements of the changing characteristics of the reflected pulse actually measure changes in the material's frequency characteristics, such as changes in loss peak frequency.

The frequency characteristics can also be measured by direct application of a signal sweeping through a wide spectrum of frequencies and spectrum analysis of the returning signals, but such an arrangement, although perhaps easier to interpret, is more difficult to measure. The pulse technique used in the invention uses a fast risetime pulse, a few nanoseconds or less, which is well understood in the art to actually include the same wide spectrum of frequencies. The reflected pulse then actually includes the desired frequency information, and a LaPlace Transform can also be used to arrive at the dipole rotation spectrum and the loss peak frequency.

However, the desired information of percent cure and viscosity can also be secured by making simple measurements on the reflected pulse.

The invention's preferred embodiment of a method of measuring cure status, that is, viscosity and percent of cure of a polymer is:

A) immersing at least one end of a transmission line into a polymer which is curing, with a capacitor connected to the immersed end of the transmission line, and the capacitor constructed so that its dielectric is the polymer into which it is immersed;

B) generating one or more step function voltage pulses and feeding the pulses to the transmission line;

C) receiving reflected pulses back from the capacitor at the end of the transmission line; and D) analyzing changing characteristics of the reflected pulses to establish the viscosity and status of cure of the polymer in which the transmission line is immersed.

In most installations pulse generator 12 and pulse detector 24 are actually included in one unit, sampling head 28. In the preferred embodiment sampling head 28 is a Hewlett Packard model 54120 Time Domain Reflectometry Oscilloscope which has a 35 ps input transient and a 20 GHz detection bandwidth.

In the preferred embodiment, incident pulse 14 is 200 millivolts, with a rise time of 35 picoseconds. The pulse length and repetition rate are not critical as long as the pulse length is long enough and the repetition rate is slow enough so that they do not result in additional pulses being generated during the 1 to 10 microseconds after the beginning of the reflected pulse when pulse analysis is being performed. The desirable pulse risetime and detector sampling resolution is in the range of 1 picosecond to 10 nanoseconds. Pulses can also be produced in bursts to produce a lower effective frequency so that data is transferred to computer 26 at a lower effective rate. Transmission line 16 can be any type of controlled impedance high frequency transmission line. As described in regard to FIG. 2 and FIG. 3, this includes both coaxial and flat ribbon, so called "Stripline", transmission lines. For the preferred embodiment, 0.86 mm, 50 ohm, miniature coaxial cable is used. Larger semi-rigid coaxial cable of 3.5 mm diameter has also been used. The length of transmission line 16 was chosen to avoid ¼ wave resonance, and the line itself must be free of connectors which add undesirable signal distortions and reflections.

Figure 2:
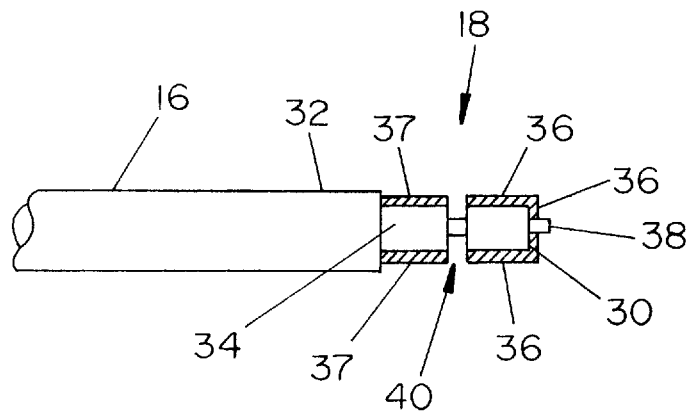
FIG. 2 is a partial cross section side view of the sensor and transmission line of the preferred embodiment of the invention.

Sensor 18, which is immersed in curing polymer 20, is essentially a miniature capacitor whose fringing electric field extends into the polymer. In the preferred embodiment it is a 1 to 2 picofarads capacitance formed near end 30 of transmission line 16, as shown in FIG. 2, but it is practical to use a capacitance in the range between 1 and 10 picofarads.

Capacitor 18 is formed on transmission line 16 by first removing a short length of outer coaxial shield 32, leaving a 2 to 3 mm length of insulating sleeve 34 exposed. The entire surface of exposed insulating sleeve 34, including end 30, is then covered with electrically conductive layers 36 and 37, which are shown in cross section. Conductive layers 36 and 37 are typically metal, although they can be other electrically conductive materials, and they are applied using conventional methods, such as evaporation or chemical plating. At this stage of construction, conductive layers 36 and 37 are joined because they have been formed as one continuous layer, and they actually create a short circuit between center conductor 38 and outer shield 32. However, the thickness of the conductive layers is not critical since there will be no significant current flow through them.

The final stage of the construction of capacitor 18 is simply forming gap 40 along the length of insulating sleeve 34 and separating conductive layers 36 and 37. Gap 40 extends through conductive layers 36 and 37 and insulating sleeve 34 to center conductor 38, and thus destroys the previously formed short circuit. Gap 40 thereby functions as the dielectric space of a capacitor whose "plates" are conductive layers 36 and 37, which are connected to inner conductor 38 and outer shield 32, respectively. Gap 40 is eventually filled by the curing polymer within which capacitor 18 is immersed. Gap 40 is formed by conventional methods such as laser cutting. If a greater capacitance is desirable, gap 40 can be formed as two interdigitated comb structures, thus increasing the effective surface of capacitor 18.

Figure 3:
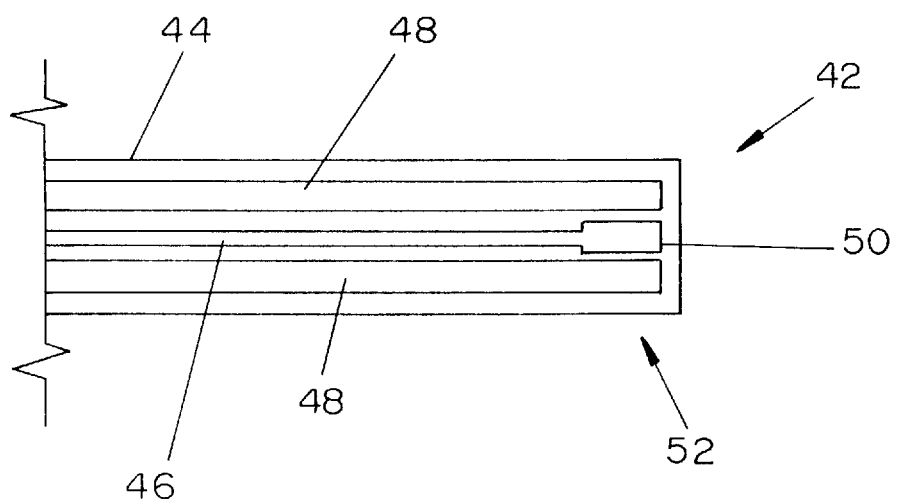
FIG. 3 is a top view of the sensor and transmission line of an alternate embodiment of the invention.

FIG. 3 is a top view of sensor 42 and transmission line 44 of an alternate embodiment of the invention. Sensor 42 and transmission line 44 are constructed as planar stripline components. Such devices are conventionally fabricated on a thin insulating substrate, and center conductor 46 is centered between coplanar ground planes 48. Transmission line 44 of the alternate embodiment of FIG. 3 is constructed with a 50 ohm impedance along the transmission path, but is fabricated with a narrower strip spacing at gap 50 at the end of transmission line 44 to form capacitor 52.

Transmission line 44 and capacitor 52 are fabricated on copper laminated teflon sheet of 0.01 to 0.05 inch thickness, and the pattern is made by photolithography and chemical etch methods. The material in gap 50 is completely etched away so that it will be replaced by the curing polymer within which capacitor 52 will be immersed. If a greater capacitance is desirable, gap 50 can be easily be made longer, thus increasing the effective surface of the capacitor. In fact, one way in which the stripline capacitor is constructed is to manufacture the capacitor section 52 of stripline transmission line 44 much longer than will be needed and to merely cut it down to secure the desired capacitance in the 1 to 10 picofarad range.

Figure 4A:
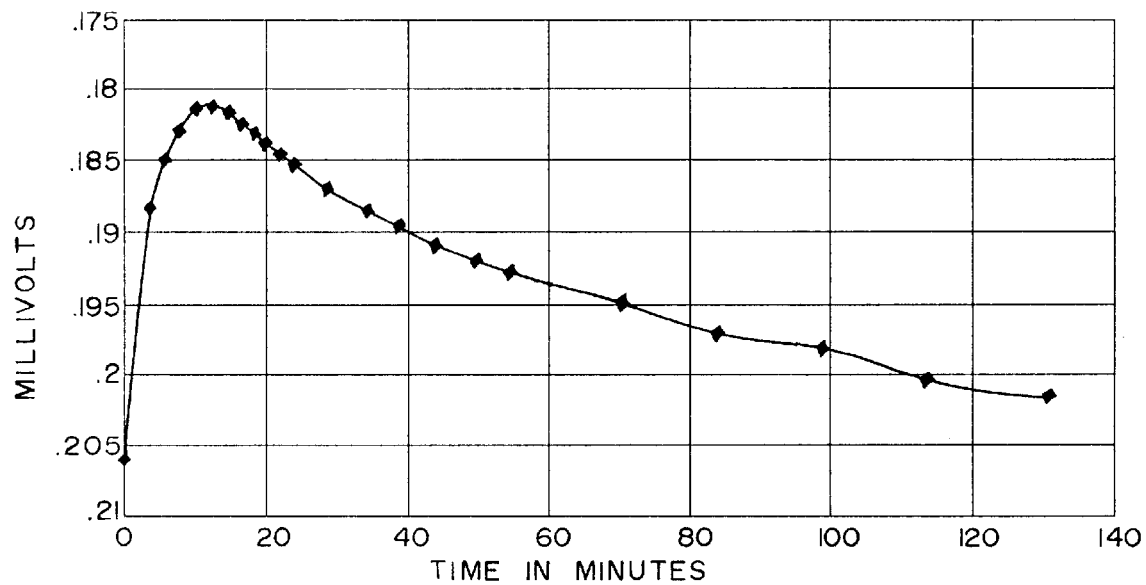
FIG. 4A and 4B are graphs of the typical variations in the reflected pulse with time as polymers cure.
Figure 4B:
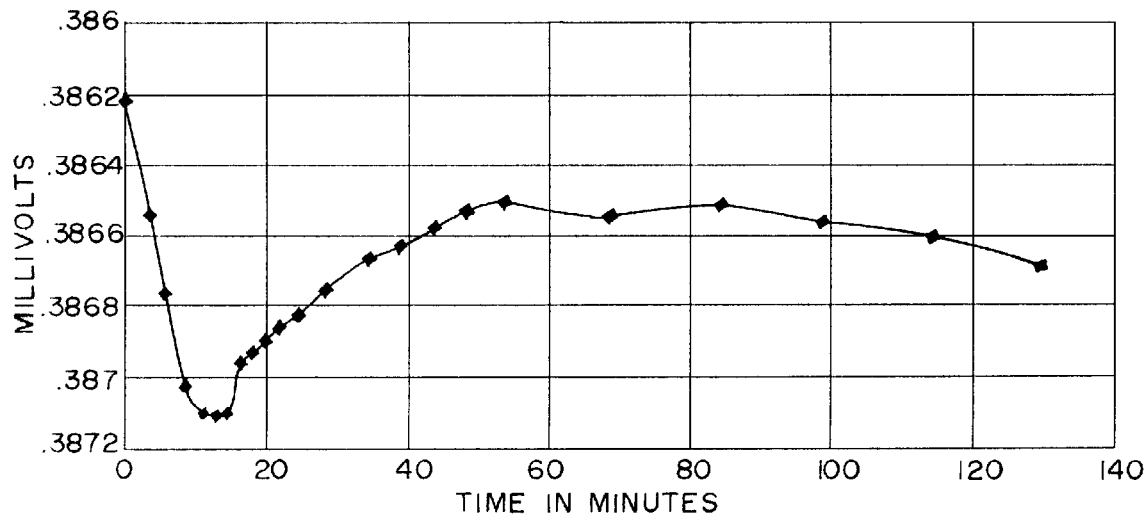

FIG. 4 is a graph of the typical variation in amplitude of reflected signal 22 (FIG. 1), in millivolts, against cure time, in minutes, as polymer 20 (FIG. 1) goes through a normal curing process. The readings for FIG. 4A were taken at 0.5 nanoseconds after the start of the reflected pulse, and are therefore close to the peak of the reflected pulse. The readings for FIG. 4B were taken at 20 nanoseconds after the start of the reflected pulse, and are therefore well into the decaying "tail" of the pulse. The material used in these tests was a mixture of EPON 825 (94%) and Epicure 3245 (6%). The curve is essentially similar for most polymers. The temperature at which the samples were held during the tests was 40 degrees centigrade. With such data available to computer 26 of FIG. 1, it is a simple task to establish when a polymer has experienced equivalent signal reductions and therefore to establish the state of cure by comparing the changing characteristics of the reflected pulses to characteristics of pulses reflected during previous controlled tests of curing polymers. This is easily accomplished by the use of computer 26 whose memory can include the previous test results. Moreover, controlled tests can be run and put into memory for any new type material so that later production testing equipment can evaluate such new materials.

However, previous test results are not a necessity. A preferred method of analysis is to measure and compare the changing amplitudes at two points on the decaying tail of the pulse for a series of reflected pulses over a period of time. As indicated in FIG. 4, typically, one of these observation points on the reflected pulses is less than 10 nanoseconds after the reflected signals begin, and the other observation point on the reflected pulses is greater than 15 nanoseconds after the reflected pulses begin. These time ranges are chosen because, as can be seen on FIG. 5, they exclude the region in which change is minimal for the viscosity indicator factor.

Figure 5:
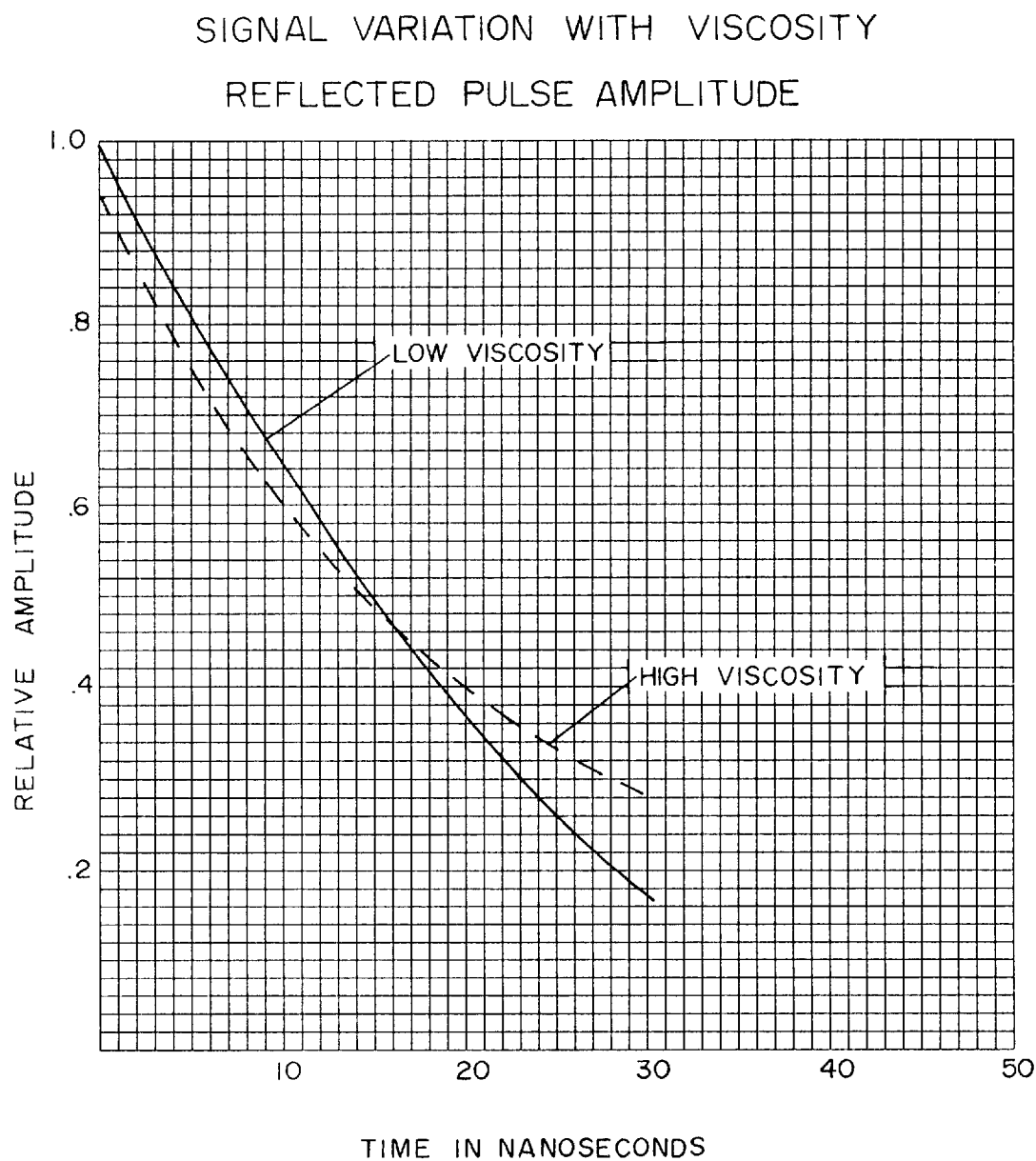
FIG. 5 is a graph showing how the decay of reflected pulses changes with viscosity.

FIG. 5 is a graph showing the manner in which the reflected pulses change as viscosity of the typical polymer changes. As can be seen from the two curves on FIG. 5, as viscosity increases as the polymer cures, the amplitudes of the reflected pulses are decreased at short times and increased at long times. A simple ratio of the amplitudes at the short time measurement point and at the long time measurement point can therefore indicate the change in viscosity of the polymer.

It is important to recognize that the curing process is usually preceded by a period in which the temperature of the polymer is increased, and during this time, when no curing is taking place but the viscosity is decreasing, the ratio of amplitude of the signal at short times to the amplitude of the signal at long times is an indicator that this process is taking place.

Figure 6:
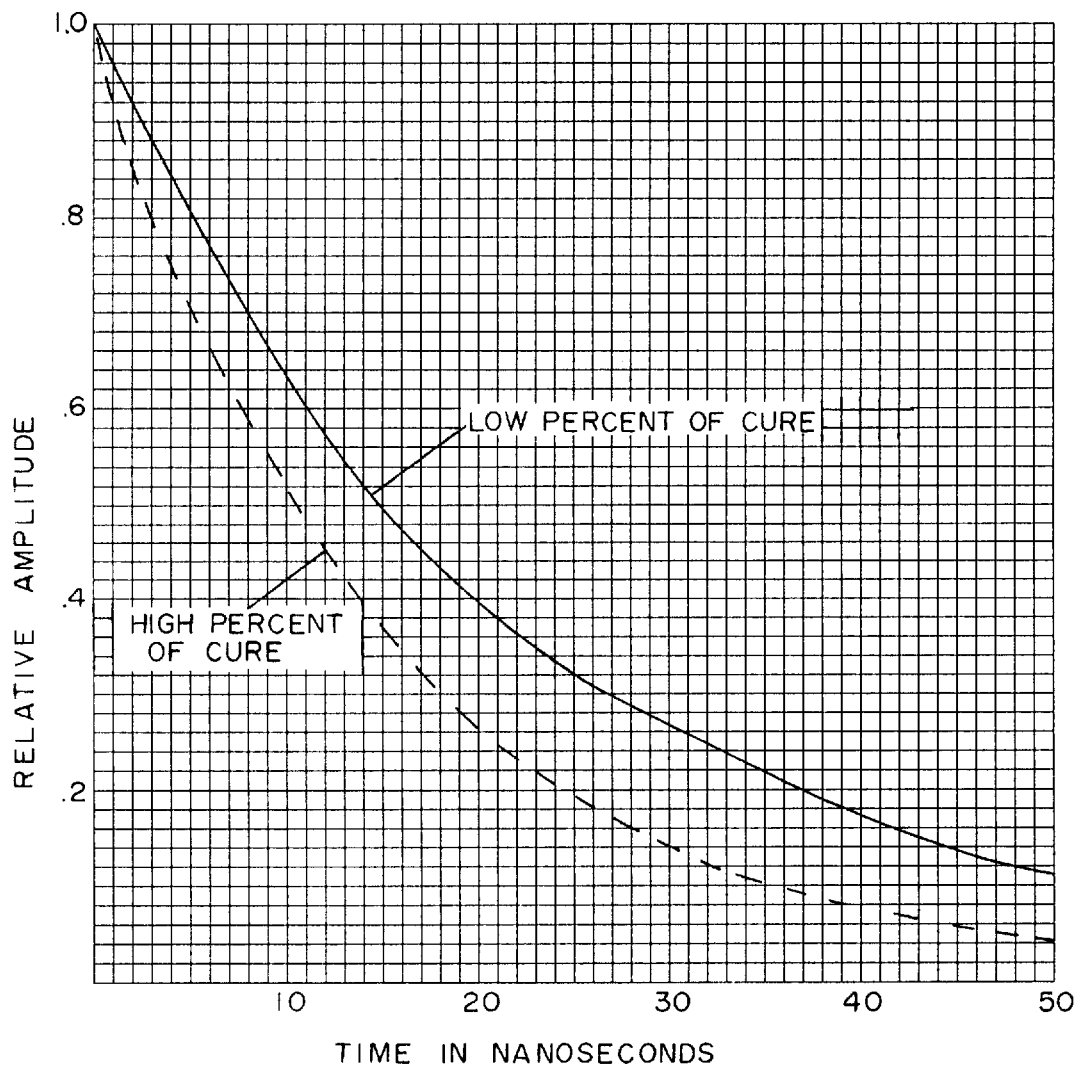
FIG. 6 is a graph showing how the reflected pulses change with reduced dipole rotation as cure progresses.

FIG. 6 is a graph showing the manner in which the reflected pulses change with reduced dipole rotation as cure of the typical polymer progresses. In this case the amplitudes of the reflected pulses are reduced at all points. In fact, the completion of the curing process can be determined when this reduction in amplitude is no longer occurring, indicating that the cure is complete. It is interesting to note that the absolute amplitude of reflected pulses at this end point of solidification should always be approximately the same for the same sensor and the same material. Therefore, in a production situation, if the amplitude reduction has stopped, but the absolute value of the amplitude is not within an appropriate range, it is an indication that there is an undesirable variation in the material.

The present invention thereby provides an accurate and reliable means to evaluate cure status of various polymers, and is capable of performing the task in either the laboratory or the production environment.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the following claims.

What is claimed as new and for which Letters Patent of the United States are desired to be secured is:

1. A method of measuring viscosity and percent of cure of a polymer comprising:

immersing at least one end of a transmission line into a polymer which is curing, with a capacitor connected to the immersed end of the transmission line, and the capacitor constructed so that its dielectric is the polymer into which it is immersed;

generating at least one step function voltage pulse and feeding it to the transmission line;

receiving a reflected pulse back from the capacitor at the end of the transmission line; and analyzing the characteristics of the reflected pulse to establish the condition of the polymer in which the transmission line is immersed.

2. The method of claim 1 wherein analyzing the reflected pulse comprises comparing characteristics of the reflected pulse to characteristics of pulses reflected during previous tests of curing polymers.

3. The method of claim 1 further including generating a series of pulses and analyzing the reflected pulses by comparing the changing amplitudes of the reflected pulses over time to determine the state of cure of the polymer.

4. The method of claim 1 further including generating a series of pulses and analyzing the reflected pulses by comparing the changing decay curves of the reflected pulses over time to determine the viscosity of the polymer.

5. The method of claim 1 further including transforming the reflected pulse into the frequency domain and analyzing the resulting frequency of the dipole rotation spectrum to determine the viscosity of the polymer.

6. The method of claim 1 further including transforming the reflected pulse into the frequency domain and analyzing the resulting loss peak frequency to determine the state of cure of the polymer.

7. The method of claim 1 wherein analyzing the reflected pulse comprises comparing over time the amplitudes of the reflected pulses at a point on the reflected pulses which is less than 10 nanoseconds after the reflected pulses begin to the amplitudes of the reflected pulses at a point on the reflected pulses which is greater than 15 nanoseconds after the reflected pulses begin.

8. An apparatus for measuring viscosity and percent of cure of a polymer comprising:

a pulse generator generating at least one step function voltage pulse;

a transmission line connected to and receiving pulses from the pulse generator, with one end of the transmission line immersed in a polymer which is curing;

a capacitor connected to the immersed end of the transmission line and also immersed in the polymer which is curing, the capacitor being constructed so that its dielectric is the polymer into which it is immersed;

a pulse detector connected to the transmission line and receiving a signal from the transmission line which is a pulse reflected from the immersed capacitor; and an analyzer means interconnected with the pulse detector, the analyzer means being capable of measuring the changes in reflected pulses as the polymer cures.

9. The apparatus of claim 8 wherein the pulse generator and the pulse detector are included in the same instrument.

10. The apparatus of claim 8 wherein the transmission line is coaxial, with an inner conductor, an insulator, and an outer conductor, and the capacitor is integrated into the transmission line by forming a gap in the insulator and outer conductor adjacent to the end of the transmission line, to separate a part of the insulator and outer conductor from the insulator and outer connector in the rest of the transmission line, and connecting the separated part of the outer conductor to the center conductor of the cable.

11. The apparatus of claim 8 wherein the transmission line is a flat line with a central conductor, insulating strips on both sides of the central conductor, and two outer conductors on the opposite sides of the insulating strips from the central conductor, and the capacitor is integrated into the transmission line by removing the insulator strips adjacent to the end of the transmission line.

12. The apparatus of claim 11 wherein the insulating strips adjacent to the end of the transmission line are narrower than the insulating strips in the rest of the transmission line so that the central conductor and the outer conductors are closer to each other adjacent to the end of the transmission line.

13. The apparatus of claim 8 wherein the capacitance of the capacitor is in the range of between 1 and 10 picofarads.

* * * * *